United States Patent
Carletti et al.

(10) Patent No.: US 9,873,715 B2
(45) Date of Patent: Jan. 23, 2018

(54) MACROLIDES USEFUL AS ANTICANCER AGENTS

(71) Applicants: PIERRE FABRE MEDICAMENT, Boulogne-Billancourt (FR); CENTRE NATIONAL DE LA RECHERCHE SCIENTIFIQUE (CNRS), Paris (FR); INSTITUT DE RECHERCHE POUR LE DEVELOPPEMENT (IRD), Marseilles (FR)

(72) Inventors: Isabelle Carletti, Toulouse (FR); Georges Massiot, Cormontreuil (FR)

(73) Assignees: PIERRE FABRE MEDICAMENT, Boulogne-Billancourt (FR); CENTRE NATIONAL DE LA RECHERCHE SCIENTIFIQUE (CNRS), Paris (FR); INSTITUT DE RECHERCHE POUR LE DEVELOPPEMENT (IRD), Marseilles (FR)

( * ) Notice: Subject to any disclaimer, the term of this patent is extended or adjusted under 35 U.S.C. 154(b) by 172 days.

(21) Appl. No.: 14/763,093

(22) PCT Filed: Jan. 24, 2014

(86) PCT No.: PCT/EP2014/051361
§ 371 (c)(1),
(2) Date: Jul. 23, 2015

(87) PCT Pub. No.: WO2014/114729
PCT Pub. Date: Jul. 31, 2014

(65) Prior Publication Data
US 2015/0376222 A1   Dec. 31, 2015

(30) Foreign Application Priority Data

Jan. 24, 2013   (FR) .................................. 13 50616

(51) Int. Cl.
*C07H 17/08* (2006.01)
*C07H 1/08* (2006.01)
(52) U.S. Cl.
CPC .............. *C07H 17/08* (2013.01); *C07H 1/08* (2013.01)

(58) Field of Classification Search
None
See application file for complete search history.

(56) References Cited

PUBLICATIONS

Faulkner, "Marine natural products," Natural Product Reports, vol. 15, No. 2, 1998, pp. 113-158, XP-000917606.
Faulkner, "Marine natural products," Natural Product Reports, vol. 18, 2001 (First published on the web Jan. 9, 2001), pp. 1-49, XP009056684.
Faulkner, "Marine natural products," Natural Product Reports, vol. 19, 2002 (First published on the web Dec. 10, 2001), pp. 1-48, XP-001068397.
International Search Report (Form PCT/ISA/210) for International Application No. PCT/EP2014/051361, dated Feb. 24, 2014.

*Primary Examiner* — Layla D Berry
*Assistant Examiner* — Bahar Craigo
(74) *Attorney, Agent, or Firm* — Birch, Stewart, Kolasch & Birch, LLP

(57) ABSTRACT

The present invention relates to a compound of the following formula (I) or to a salt, hydrate, or pharmaceutically acceptable solvate thereof, in which R is a monosaccharide or disaccharide residue. The hydroxyl functions of the monosaccharide or disaccharide residue are, independently, optionally substituted for a ($C_1$-$C_6$) alkyl or —C(O)NH—($C_1$-$C_6$) alkyl group. The invention also relates to the method for preparing said compound, to a pharmaceutical composition containing same, and to the use thereof as a drug, particularly for cancer treatment.

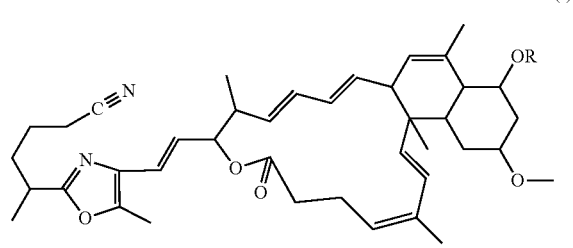

20 Claims, No Drawings

MACROLIDES USEFUL AS ANTICANCER AGENTS

The present invention relates to macrolide-type molecules extracted from a sponge and analogues thereof, a method of extraction and hemisynthesis and the use of said compounds as a medicine, in particular in the treatment of cancer.

Since several decades ago, marine sponges have become the focus of numerous studies following the disclosure of their production of bioactive secondary metabolites, in particular alkaloids.

The Inventors have thus been able to isolate a novel family of molecules from a sponge of the family Verongidae, such as a *Suberea* sp. sponge, for example *Suberea creba*, from New Caledonia, which has anticancer activity.

The subject matter of the present invention is thus a compound of the following formula (I):

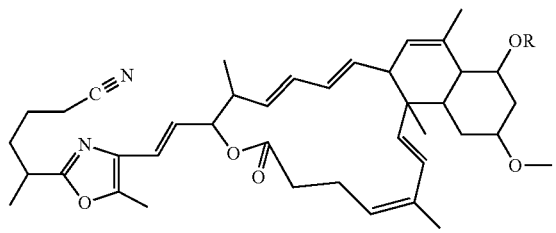

(I)

or a pharmaceutically acceptable salt, hydrate or solvate thereof,
in which R is a monosaccharide or disaccharide residue, the hydroxyl functional groups of the monosaccharide or disaccharide residue being, independently of each other, optionally substituted with a $(C_1-C_6)$alkyl group, preferably a methyl group, or a —C(O)NH—$(C_1-C_6)$alkyl group, preferably a —C(O)NHMe group.

In the present invention, by "pharmaceutically acceptable" is meant that which is useful in the preparation of a pharmaceutical composition that is generally safe, nontoxic and neither biologically nor otherwise undesirable and that is acceptable for both veterinary and human pharmaceutical use.

By "pharmaceutically acceptable salt, hydrate or solvate" of a compound is meant a salt, hydrate or solvate that is pharmaceutically acceptable, as defined herein, and that has the desired pharmacological activity of the parent compound.

Pharmaceutically acceptable salts comprise in particular:

(1) pharmaceutically acceptable acid addition salts formed with pharmaceutically acceptable inorganic acids such as hydrochloric acid, hydrobromic acid, sulfuric acid, nitric acid, phosphoric acid and the like; or formed with pharmaceutically acceptable organic acids such as acetic acid, benzenesulfonic acid, benzoic acid, camphorsulfonic acid, citric acid, ethanesulfonic acid, fumaric acid, glucoheptonic acid, gluconic acid, glutamic acid, glycolic acid, hydroxynaphthoic acid, 2-hydroxyethanesulfonic acid, lactic acid, maleic acid, malic acid, mandelic acid, methanesulfonic acid, muconic acid, 2-naphthalenesulfonic acid, propionic acid, salicylic acid, succinic acid, dibenzoyl-L-tartaric acid, tartaric acid, p-toluenesulfonic acid, trimethylacetic acid, trifluoroacetic acid and the like, and (2) pharmaceutically acceptable base addition salts formed when an acid proton present in the parent compound is replaced with a metal ion, for example an alkaline metal ion, an alkaline-earth metal ion or an aluminum ion; or coordinates with a pharmaceutically acceptable organic base such as diethanolamine, ethanolamine, N-methylglucamine, triethanolamine, tromethamine and the like; or with a pharmaceutically acceptable inorganic base such as aluminum hydroxide, calcium hydroxide, potassium hydroxide, sodium carbonate, sodium hydroxide and the like.

By "$(C_1-C_6)$alkyl" group is meant, in the context of the present invention, a saturated linear or branched monovalent hydrocarbon chain comprising 1 to 6 carbon atoms, preferably 1 to 4 carbon atoms. For example, mention may be made of the following groups: methyl, ethyl, propyl, isopropyl, butyl, isobutyl, sec-butyl, tert-butyl, pentyl or hexyl. Preferably it will be a methyl group.

By "monosaccharide" is meant, in the context of the present invention, an aldose (a saccharide bearing an aldehyde functional group at the terminal position, that is, on carbon atom 1), and more particularly an aldohexose (a saccharide with 6 carbon atoms) or an aldopentose (a saccharide with 5 carbon atoms), preferably an aldohexose. It will thus be in particular allose, altrose, glucose, mannose, gulose, idose, galactose, talose, ribose, arabinose, xylose or lyxose, in D or L form. The monosaccharide will be preferably in a cyclized form, in particular a pyranic form (a 6-member ring). In this case, the aldehyde functional group borne by the saccharide is in a hemiacetal form, also called a pseudoaldehyde functional group.

By "disaccharide" is meant, in the context of the present invention, a molecule resulting from the condensation of two monosaccharides as defined above, such a condensation being accompanied by the loss of a water molecule. This condensation reaction is carried out in the context of the present invention between the aldehyde (or pseudoaldehyde) functional group of one of the monosaccharides and a hydroxy (OH) functional group of the other monosaccharide. The resulting disaccharide has thus one and only one aldehyde (or pseudoaldehyde) functional group. Preferably, the disaccharide will result from the condensation of the aldehyde (or pseudoaldehyde) functional group of an aldopentose and a hydroxy (OH) functional group of an aldohexose.

By "monosaccharide or disaccharide residue" is meant, in the context of the present invention, the part of a monosaccharide or disaccharide, as defined above, that is connected to the rest of the molecule via its carbon atom 1 following a condensation reaction between the aldehyde (or pseudoaldehyde) functional group of the monosaccharide or disaccharide and a hydroxy (OH) functional group.

In the case of an aldohexose-type monosaccharide residue in pyranic form, it will thus be the following group:

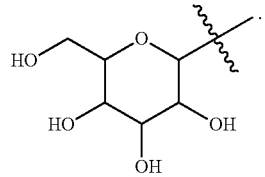

Preferably, the R group will be the following group:

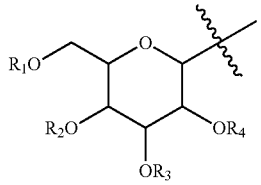

in which the $R_1$ to $R_4$ groups are, independently of each other, a hydrogen atom, a $(C_1-C_6)$alkyl group, preferably a methyl group, a —C(O)NH—$(C_1-C_6)$alkyl group, preferably a —C(O)NHMe group, or a monosaccharide residue of the following formula:

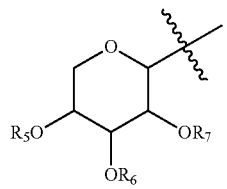

in which the $R_5$ to $R_7$ groups are, independently of each other, a hydrogen atom, a $(C_1-C_6)$alkyl group, preferably a methyl group, or a —C(O)NH—$(C_1-C_6)$alkyl group, preferably a —C(O)NHMe group, and only one $R_1$ to $R_4$ group may be a monosaccharide residue.

Advantageously, $R_1=R_4=$Me, $R_2=$H and $R_3=$H or a monosaccharide residue of the following formula:

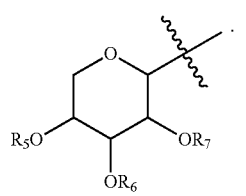

The R group may in particular be a:

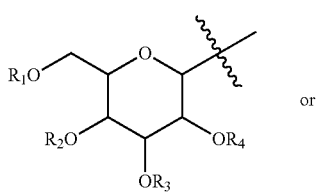

or

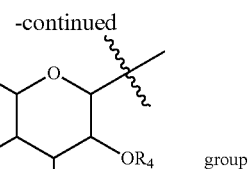

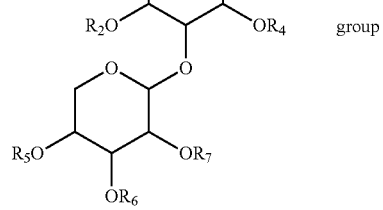

group in which:
$R_1$ to $R_4$ are, independently of each other, a hydrogen atom, a $(C_1-C_6)$alkyl group, preferably a methyl group, or a —C(O)NH—$(C_1-C_6)$alkyl group, preferably a —C(O)NHMe group; in particular a hydrogen atom or a $(C_1-C_6)$alkyl group; in particular H or Me, and
$R_5$ to $R_7$ are, independently of each other, a hydrogen atom, a $(C_1-C_6)$alkyl group, preferably a methyl group, or a —C(O)NH—$(C_1-C_6)$alkyl group, preferably a —C(O)NHMe group; in particular H, Me or a —C(O)NHMe group.

The R group may more particularly be a group selected from:

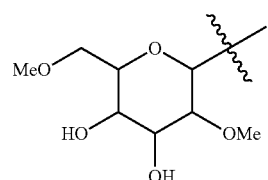

,

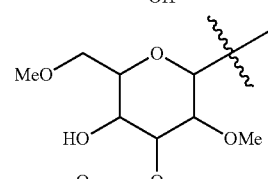

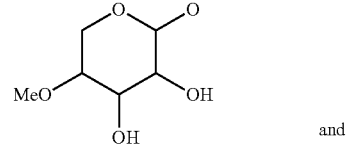

and

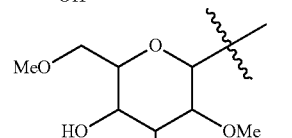

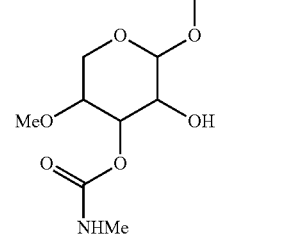

Given the number of asymmetrical carbon atoms present on said compounds of formula (I), the latter may take various configurations. A compound according to the invention may in particular be a compound having a stereochemistry defined by its method of preparation, in particular obtainable by a method comprising the following successive steps:
(i) one or more macerations of a lyophilizate of a sponge of the family Verongidae, such as a *Suberea* sp. sponge, for example *Suberea creba*, with a water/ethanol solution (in particular 10/90 water/ethanol, v/v); followed by filtration to yield a filtrate; then concentration of said filtrate to yield an aqueous syrup,
(ii) addition of water to the aqueous syrup obtained in the preceding step (i), one or more extractions with ethyl acetate and separation of the resulting aqueous and organic phases; concentration of the organic phase or of the combined organic phases thus obtained to yield a dry extract,
(iii) isolation from the dry extract obtained in the preceding step (ii) of a compound of formula (I) with R being:

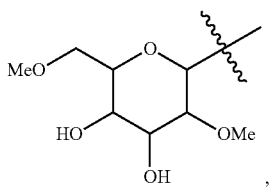

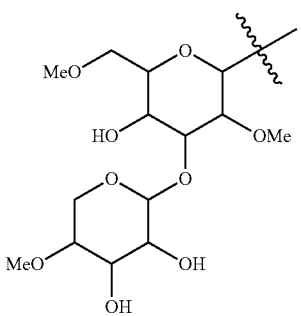

or

-continued

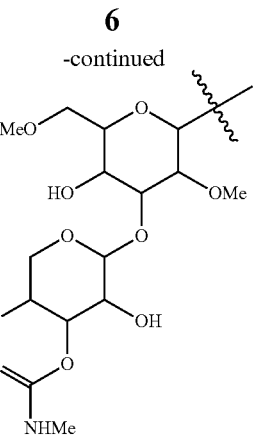

(iv) optionally hydrolysis of the compound of formula (I) obtained in the preceding step to yield a compound of the following formula (II):

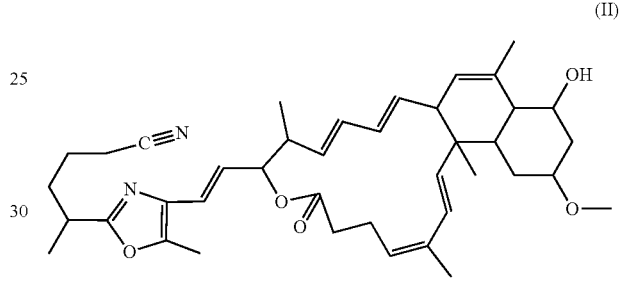

(II)

and substitution of the OH functional group of the compound of formula (II) to give a compound of formula (I) as defined above, and
(v) optionally salification, hydration or solvation of the compound of formula (I) obtained in the preceding step (iii) or (iv) to yield a pharmaceutically acceptable salt, hydrate or solvate thereof.

In the context of this method, the sponge of the family Verongidae used, such as a *Suberea* sp. sponge, for example *Suberea creba*, may originate from New Caledonia.

The compound of formula (I) may be selected more particularly from:

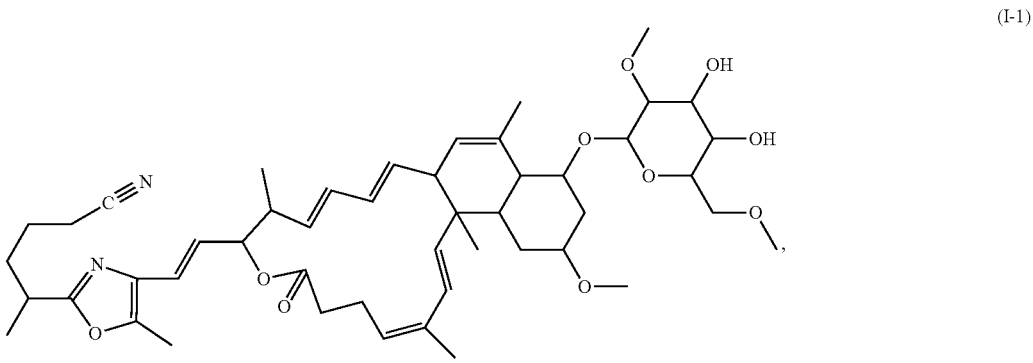

(I-1)

-continued

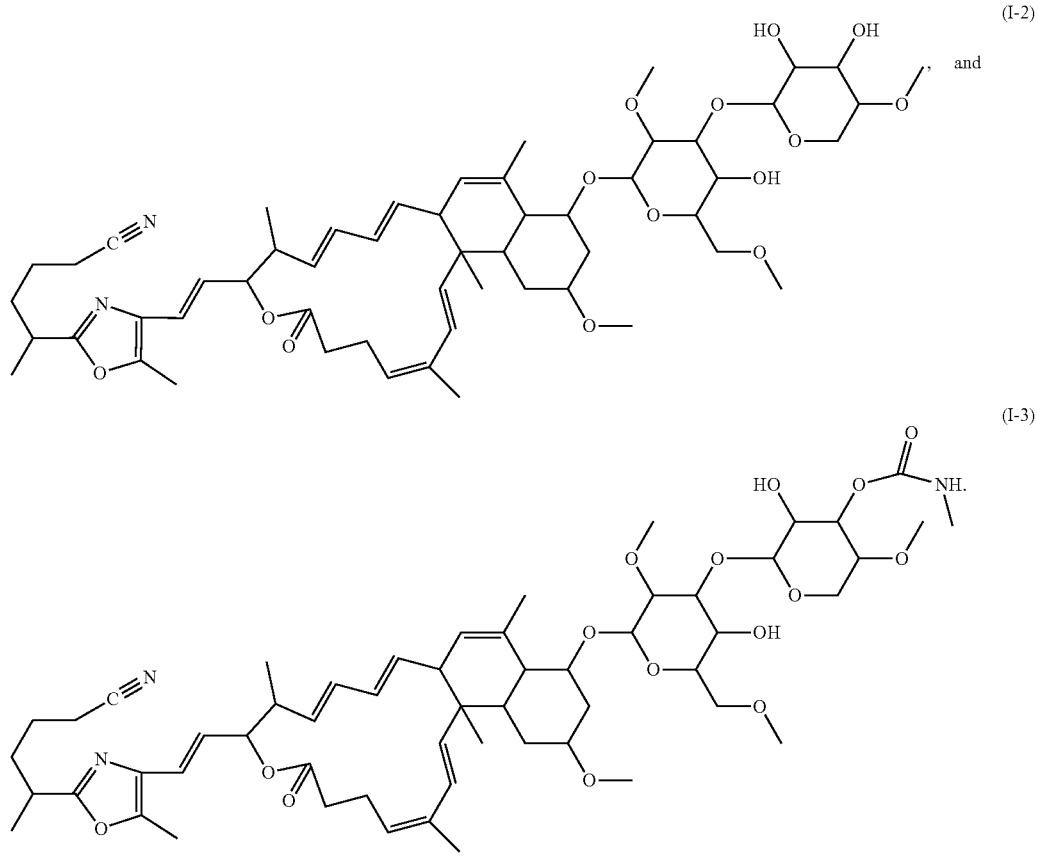

Another subject matter of the present invention is a compound of formula (I) as defined above for use as a medicine, in particular in the treatment of cancer.

The present invention also relates to the use of a compound of formula (I) as disclosed above for the preparation of a medicine, in particular in the treatment of cancer.

The invention also relates to a method for treating cancer comprising the administration to a person in need thereof of an effective dose of a compound of formula (I) as defined above.

The cancer may be in particular solid or non-solid tumors, such as melanoma, colorectal cancer, lung cancer, prostate cancer, liver cancer, breast cancer, uterine cancer, stomach cancer, pancreatic cancer, bladder cancer, ovarian cancer, head and neck cancers, brain cancer, leukemia, lymphomas (including Burkitt lymphoma) and myelomas.

Another subject matter of the present invention is a pharmaceutical composition comprising at least one compound of formula (I) as defined above and a pharmaceutically acceptable excipient.

The pharmaceutical compositions of the invention may be formulated, for example, for intravenous or oral administration.

The compounds of the invention as active ingredients may be used in doses between 0.01 mg and 1000 mg per day, for example in a single dose.

In a particular embodiment of the invention, the pharmaceutical composition is used as a medicine, for example in the treatment of cancer.

Another subject matter of the present invention is a method for the preparation of a compound as defined above, comprising the following successive steps:

(i) one or more macerations of a lyophilizate of a sponge of the family Verongidae, such as a *Suberea* sp. sponge, for example *Suberea creba*, with a water/ethanol solution (in particular 10/90 water/ethanol, v/v); followed by filtration to yield a filtrate; then concentration of said filtrate to yield an aqueous syrup, (ii) addition of water to the aqueous syrup obtained in the preceding step (i), one or more extractions with ethyl acetate and separation of the resulting aqueous and organic phases; concentration of the organic phase or of the combined organic phases thus obtained to yield a dry extract, (iii) isolation from the dry extract obtained in the preceding step (ii) of a compound of formula (I) with R being:

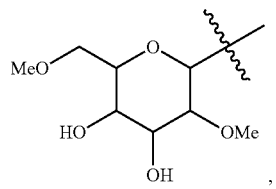

-continued

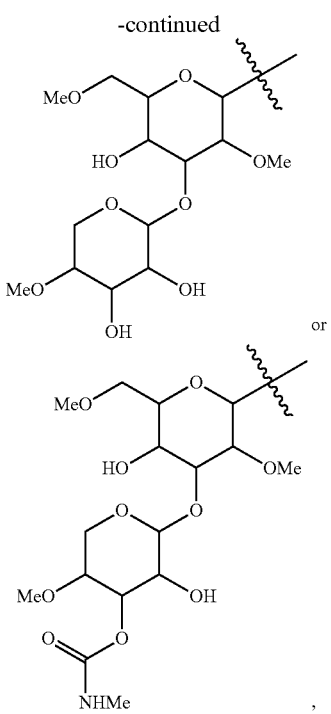

(iv) optionally hydrolysis of the compound of formula (I) obtained in the preceding step to yield a compound of the following formula (II):

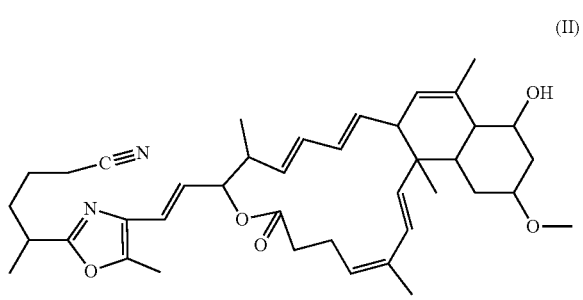

(II)

and substitution of the OH functional group of the compound of formula (II) to give a compound of formula (I) as defined above, and (v) optionally salification, hydration or solvation of the compound of formula (I) obtained in the preceding step (iii) or (iv) to yield a pharmaceutically acceptable salt, hydrate or solvate thereof.

In the context of this method, the sponge of the family Verongidae used, such as a *Suberea* sp. sponge, for example *Suberea creba*, may originate from New Caledonia.

The maceration step (i) may be carried out 1 to 5 times, in particular 4 times.

The extraction step (ii) may be carried out 1 to 5 times, in particular 3 times.

Isolation of the compound according to the invention in step (iii) may be carried out in particular by chromatography on silica gel. The product obtained may then be purified by techniques well-known to the skilled person, and in particular by high-performance liquid chromatography (HPLC).

The hydrolysis and substitution steps of step (iv) and the salification, hydration and solvation steps of step (v) may be carried out by techniques well-known to the skilled person.

The compound thus obtained may be separated from the reaction medium by methods well-known to the skilled person, such as, for example, by extraction, evaporation of the solvent or by precipitation and filtration.

The compound may in addition be purified if necessary by techniques well-known to the skilled person, like by recrystallization if the compound is crystalline, by distillation, by column chromatography on silica gel or by high-performance liquid chromatography (HPLC).

The invention is disclosed more specifically, in a non-limiting manner, in the following examples.

EXAMPLES

In the examples below, the following abbreviations were used:

ACN Acetonitrile
ESIMS Electrospray ionization mass spectrometry
HPLC High-performance liquid chromatography
HRESITOFMS High-resolution electrospray ionization time-of-flight mass spectrometry
NMR Nuclear magnetic resonance 1. Preparation of the Compounds of Formula (I)

Samples of the *Suberea* sp. marine sponge, for example *Suberea creba*, were collected in New Caledonia in 2000 and then freeze-dried to yield 150 g of lyophilizate. This lyophilizate was successively macerated four times for 1 hour with shaking in a 10:90 water/alcohol solution (meaning 10% water and 90% ethanol by volume). The filtrates obtained (4 liters in total) were combined, filtered and concentrated using a rotary evaporator until an aqueous syrup was obtained. Said aqueous syrup was successively partitioned three times with ethyl acetate. The organic phases were combined and dried until a dry crude organic extract was obtained (2.55 g).

The organic extract inhibited cell growth by about 45% at concentrations of both 10 µg/ml and 1 µg/ml (results obtained were 43.4% and 46.7%, respectively) on the WM266-4 human metastatic melanoma cell line, thus showing a cytostatic effect.

"Flash" (or "stepwise") chromatography on a normal silica column was carried out on the crude organic extract with increasing polarity elution with cyclohexane and ethyl acetate, then ethyl acetate and methanol, in order to obtain 13 fractions. The fractions were all tested on the WM-266-4 line. Only fractions no. 6 and no. 8 had a percent inhibition of 53% and 47%, respectively, at 10 µg/ml.

The final purifications were carried out by preparative reversed-phase HPLC (RP C18) using a water/acetonitrile gradient in order to obtain the following three active molecules:

| | Molecule (I-1) | Molecule (I-2) | Molecule (I-3) |
|---|---|---|---|
| $UV_{max}$ (Water-ACN) | 235 nm (broad) | 235 nm (broad) | 235 nm (broad) |
| Amount | 2 mg | 3.1 mg | 4.5 mg |
| Yield relative to the sponge lyophilizate | 0.0013% | 0.0021% | 0.0030% |

Molecule (I-1):

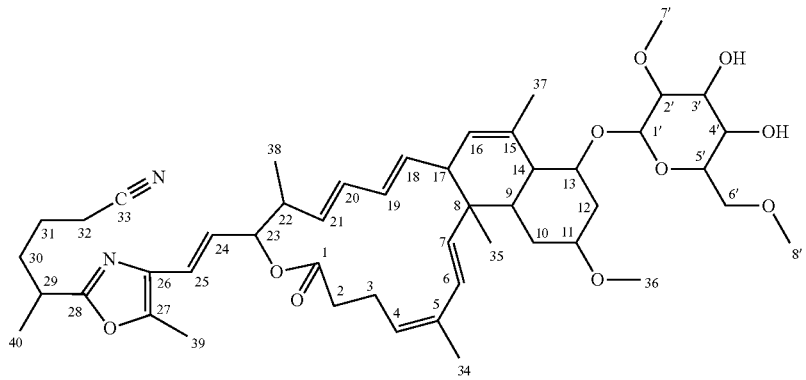 [SMILES: COCC1OC(OC2CC(OC)CC3C2C(C)=CC2/C=C/C=C/C(C)C(/C=C/c4nc(C(C)CCCC#N)oc4C)OC(=O)CC/C=C(C)\C=C\C23C)C(OC)C(O)C1O]

Molecular formula: $C_{48}H_{68}N_2O_{10}$—Exact mass: 832.49
ESIMS m/z: 833.7 $(M+H)^+$ $^1$H NMR (500 MHz, METHANOL-$d_4$) δ=6.50 (1H, d, J=16.4 Hz, H-6), 6.36 (1H, d, J=15.4 Hz, H-25), 6.17 (1H, dd, J=15.4 Hz, J=8.2 Hz, H-24), 6.03 (1H, t, J=10.4 Hz, H-20), 5.98 (1H, t, J=10.4 Hz, H-19), 5.75 (1H, dd, J=14.2 Hz, J=9.8 Hz, H-18), 5.56 (1H, d, J=16.4 Hz, H-7), 5.25 (2H, dd, J=14.2 Hz, J=9.8 Hz, H-21), 5.23 (1H, m, H-16), 5.17 (1H, dd, J=9.0 Hz, J=4.9 Hz, H-4), 5.11 (1H, dd, J=10.1 Hz, J=8.5 Hz, H-23), 3.67 (1H, dd, J=10.7 Hz, J=2.2 Hz, H-6'), 3.60 (3H, s, H-7'), 3.56 (1H, dd, J=10.7 Hz, J=5.0 Hz, H-6'), 3.48 (1H, m, H-4'), 3.48 (1H, m, H-2''), 3.42 (1H, t, J=9.3 Hz, H-3'), 3.38 (1H, m, H-11), 3.35 (3H, s, H-8'), 3.33 (1H, m, H-5'), 3.31 (3H, s, H-36), 3.09 (1H, dd, J=9.1 Hz, J=7.9 Hz, H-2'), 2.92 (1H, m, H-29), 2.80 (1H, m, H-17), 2.67 (1H, s, H-14), 2.45 (1H, m, H-3), 2.33 (2H, td, J=7.3 Hz, J=3.8 Hz, H-32), 2.28 (1H, m, H-2), 2.28 (1H, m, H-22), 2.27 (3H, s, H-39), 2.20 (1H, d, J=12.9 Hz, H-12), 2.14 (1H, m, H-3), 2.08 (1H, td, J=13.6 Hz, J=3.2 Hz, H-2), 1.87 (1H, m, H-9), 1.87 (1H, m, H-10), 1.87 (1H, m, H-30), 1.75 (3H, s, H-34), 1.72 (1H, m, H-30), 1.64 (2H, m, H-31), 1.63 (3H, s, H-37), 1.33 (1H, t, J=12.0 Hz, H-10), 1.30 (3H, d, J=6.9 Hz, H-40), 1.06 (1H, m, H-12), 0.98 (3H, d, J=6.6 Hz, H-38).

$^{13}$C NMR (126 MHz, CDCl$_3$) δ=172.6 (C-1), 165.3 (C-28), 145.1 (C-27), 139.1 (C-7), 136.3 (C-18), 133.8 (C-21), 133.3 (C-5), 132.4 (C-20), 132.0 (C-26), 129.8 (C-19), 128.4 (C-15), 127.5 (C-16), 127.1 (C-6), 126.4 (C-4), 126.3 (C-24), 122.5 (C-25), 119.4 (C-33), 104.7 (C-1'), 82 (C-2'), 77.5 (C-23), 77.1 (C-13), 75.5 (C-11), 74.8 (C-5'), 71.7 (C-6'), 68.9 (C-4'), 61.1 (C-7'), 59.4 (C-8'), 55.8 (C-36), 48.5 (C-17), 44.0 (C-22), 40.8 (C-8), 40.7 (C-9), 40.3 (C-14), 35.2 (C-2), 33.8 (C-30), 33.2 (C-29), 32.6 (C-12), 32.0 (C-10), 30.9 (C-35), 24.1 (C-3), 23.2 (C-31), 20.8 (C-37), 20.2 (C-34), 18.6 (C-40), 17.1 (C-32).

Molecule (I-2):

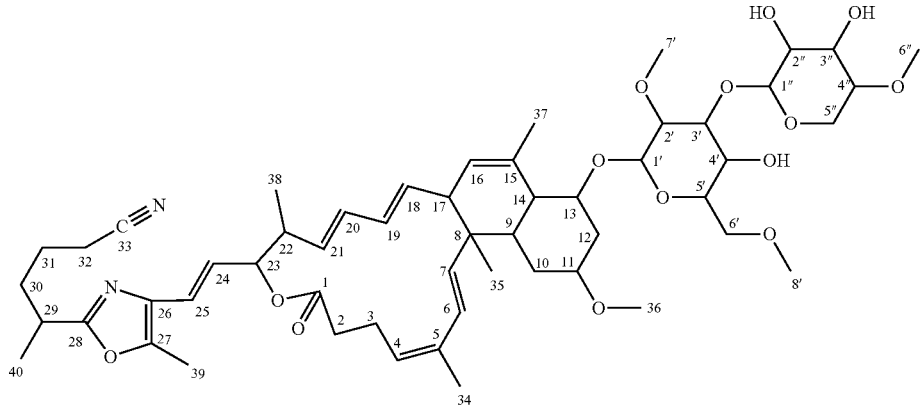 [SMILES: COCC1OC(OC2CC(OC)CC3C2C(C)=CC2/C=C/C=C/C(C)C(/C=C/c4nc(C(C)CCCC#N)oc4C)OC(=O)CC/C=C(C)\C=C\C23C)C(OC)C(OC2OCC(OC)C(O)C2O)C1O]

Molecular formula: $C_{54}H_{78}N_2O_{14}$—Exact mass: 978.55
ESIMS m/z: 979.7 $(M+H)^+$
HRESITOFMS m/z: 1001.53519 $(M+Na)^+$, calculated for $C_{54}H_{78}N_2O_{14}Na_1$ m/z 1001.53453

$^1$H NMR (500 MHz, METHANOL-$d_4$) δ=6.50 (1H, d, J=16.4 Hz, H-6), 6.36 (1H, d, J=15.4 Hz, H-25), 6.17 (1H, dd, J=15.4 Hz, J=8.2 Hz, H-24), 6.03 (1H, t, J=10.4 Hz, H-20), 5.98 (1H, t, J=10.4 Hz, H-19), 5.75 (1H, dd, J=14.2 Hz, J=9.8 Hz, H-18), 5.56 (1H, d, J=16.4 Hz, H-7), 5.25 (2H, dd, J=14.2 Hz, J=9.8 Hz, H-21), 5.23 (1H, m, H-16), 5.17 (1H, dd, J=9.0 Hz, J=4.9 Hz, H-4), 5.11 (1H, dd, J=10.1 Hz, J=8.5 Hz, H-23), 4.82 (1H, s, H-8''), 4.81 (1H, t, J=8.8 Hz, H-3''), 4.44 (1H, d, J=7.6 Hz, H-1''), 4.40 (1H, q, J=2.8 Hz,

H-13), 4.36 (1H, d, J=7.9 Hz, H-1'), 4.08 (1H, dd, J=11.2 Hz, J=4.6 Hz, H-5"), 3.67 (1H, dd, J=10.7 Hz, J=2.2 Hz, H-6'), 3.60 (3H, s, H-7'), 3.56 (1H, dd, J=10.7 Hz, J=5.0 Hz, H-6'), 3.48 (1H, m, H-4'), 3.48 (1H, m, H-2"), 3.42 (1H, t, J=9.3 Hz, H-3'), 3.38 (1H, m, H-11), 3.38 (1H, m, H-4"), 3.35 (3H, s, H-8'), 3.33 (1H, m, H-5'), 3.33 (1H, m, H-5"), 3.31 (3H, s, H-36), 3.09 (1H, dd, J=9.1 Hz, J=7.9 Hz, H-2'), 2.92 (1H, m, H-29), 2.80 (1H, m, H-17), 2.67 (1H, s, H-14), 2.45 (1H, m, H-3), 2.33 (2H, td, J=7.3 Hz, J=3.8 Hz, H-32), 2.28 (1H, m, H-2), 2.28 (1H, m, H-22), 2.27 (3H, s, H-39), 2.20 (1H, d, J=12.9 Hz, H-12), 2.14 (1H, m, H-3), 2.08 (1H, td, J=13.6 Hz, J=3.2 Hz, H-2), 1.87 (1H, m, H-9), 1.87 (1H, m, H-10), 1.87 (1H, m, H-30), 1.75 (3H, s, H-34), 1.72 (1H, m, H-30), 1.64 (2H, m, H-31), 1.63 (3H, s, H-37), 1.33 (1H, t, J=12.0 Hz, H-10), 1.30 (3H, d, J=6.9 Hz, H-40), 1.06 (1H, m, H-12), 0.98 (3H, d, J=6.6 Hz, H-38).

$^{13}$C NMR (126 MHz, CDCl$_3$) δ=172.6 (C-1), 165.3 (C-28), 145.1 (C-27), 139.1 (C-7), 136.3 (C-18), 133.8 (C-21), 133.3 (C-5), 132.4 (C-20), 132.0 (C-26), 129.8 (C-19), 128.4 (C-15), 127.5 (C-16), 127.1 (C-6), 126.4 (C-4), 126.3 (C-24), 122.5 (C-25), 119.4 (C-33), 104.7 (C-1'), 102.6 (C-1"), 86.9 (C-3"), 82 (C-2'), 77.5 (C-23), 77.1 (C-13), 76.7 (C-3"), 76.6 (C-4"), 75.5 (C-11), 74.8 (C-5'), 72.5 (C-2"), 71.7 (C-6'), 68.9 (C-4'), 63.3 (C-5"), 61.1 (C-7'), 59.4 (C-8'), 58.8 (C-6"), 55.8 (C-36), 48.5 (C-17), 44.0 (C-22), 40.8 (C-8), 40.7 (C-9), 40.3 (C-14), 35.2 (C-2), 33.8 (C-30), 33.2 (C-29), 32.6 (C-12), 32.0 (C-10), 30.9 (C-35), 24.1 (C-3), 23.2 (C-31), 20.8 (C-37), 20.2 (C-34), 18.6 (C-40), 17.1 (C-32).

Molecule (I-3):

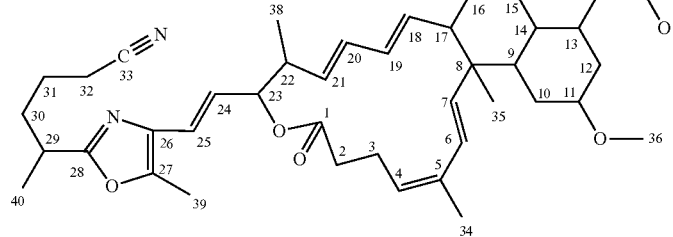

Molecular formula: C$_{56}$H$_{81}$N$_3$O$_{15}$—Exact mass: 1035.57
ESIMS m/z: 1038.8 (M+H)$^+$ $^1$H NMR (500 MHz, METHANOL-d$_4$) δ=6.50 (1H, d, J=16.4 Hz, H-6), 6.36 (1H, d, J=15.4 Hz, H-25), 6.17 (1H, dd, J=15.4 Hz, J=8.2 Hz, H-24), 6.03 (1H, t, J=10.4 Hz, H-20), 5.98 (1H, t, J=10.4 Hz, H-19), 5.75 (1H, dd, J=14.2 Hz, J=9.8 Hz, H-18), 5.56 (1H, d, J=16.4 Hz, H-7), 5.25 (2H, dd, J=14.2 Hz, J=9.8 Hz, H-21), 5.23 (1H, m, H-16), 5.17 (1H, dd, J=9.0 Hz, J=4.9 Hz, H-4), 5.11 (1H, dd, J=10.1 Hz, J=8.5 Hz, H-23), 4.82 (1H, s, H-8"), 4.81 (1H, t, J=8.8 Hz, H-3"), 4.44 (1H, d, J=7.6 Hz, H-1"), 4.40 (1H, q, J=2.8 Hz, H-13), 4.36 (1H, d, J=7.9 Hz, H-1'), 4.08 (1H, dd, J=11.2 Hz, J=4.6 Hz, H-5"), 3.67 (1H, dd, J=10.7 Hz, J=2.2 Hz, H-6'), 3.60 (3H, s, H-7'), 3.56 (1H, dd, J=10.7 Hz, J=5.0 Hz, H-6'), 3.48 (1H, m, H-4'), 3.48 (1H, m, H-2"), 3.42 (1H, t, J=9.3 Hz, H-3'), 3.41 (3H, s, H-6"), 3.38 (1H, m, H-11), 3.38 (1H, m, H-4"), 3.35 (3H, s, H-8'), 3.33 (1H, m, H-5'), 3.33 (1H, m, H-5"), 3.31 (3H, s, H-36), 3.09 (1H, dd, J=9.1 Hz, J=7.9 Hz, H-2'), 2.92 (1H, m, H-29), 2.82 (3H, d, J=5.0 Hz, H-9"), 2.80 (1H, m, H-17), 2.67 (1H, s, H-14), 2.45 (1H, m, H-3), 2.33 (2H, td, J=7.3 Hz, J=3.8 Hz, H-32), 2.28 (1H, m, H-2), 2.28 (1H, m, H-22), 2.27 (3H, s, H-39), 2.20 (1H, d, J=12.9 Hz, H-12), 2.14 (1H, m, H-3), 2.08 (1H, td, J=13.6 Hz, J=3.2 Hz, H-2), 1.87 (1H, m, H-9), 1.87 (1H, m, H-10), 1.87 (1H, m, H-30), 1.75 (3H, s, H-34), 1.72 (1H, m, H-30), 1.64 (2H, m, H-31), 1.63 (3H, s, H-37), 1.33 (1H, t, J=12.0 Hz, H-10), 1.30 (3H, d, J=6.9 Hz, H-40), 1.06 (1H, m, H-12), 0.98 (3H, d, J=6.6 Hz, H-38).

$^{13}$C NMR (126 MHz, CDCl$_3$) δ=172.6 (C-1), 165.3 (C-28), 157.1 (C-6"), 145.1 (C-27), 139.1 (C-7), 136.3 (C-18), 133.8 (C-21), 133.3 (C-5), 132.4 (C-20), 132.0 (C-26), 129.8 (C-19), 128.4 (C-15), 127.5 (C-16), 127.1 (C-6), 126.4 (C-4), 126.3 (C-24), 122.5 (C-25), 119.4 (C-33), 104.7 (C-1'), 102.6 (C-1"), 86.9 (C-3"), 82 (C-2'), 77.5 (C-23), 77.1 (C-13), 76.7 (C-3"), 76.6 (C-4"), 75.5 (C-11), 74.8 (C-5'), 72.5 (C-2"), 71.7 (C-6'), 68.9 (C-4'), 63.3 (C-5"), 61.1 (C-7'), 59.4 (C-8'), 58.8 (C-8"), 55.8 (C-36), 48.5 (C-17), 44.0 (C-22), 40.8 (C-8), 40.7 (C-9), 40.3 (C-14), 35.2 (C-2), 33.8 (C-30), 33.2 (C-29), 32.6 (C-12), 32.0 (C-10), 30.9 (C-35), 27.7 (C-7"), 24.1 (C-3), 23.2 (C-31), 20.8 (C-37), 20.2 (C-34), 18.6 (C-40), 17.1 (C-32).

2. Biological Activity of the Compounds of Formula (I)

Molecules (I-1), (I-2) and (I-3) were identified during a test of antiproliferative activity on a metastatic melanoma cell line, WM266-4. They proved very cytotoxic on a set of seven other tumor lines (A549: human lung adenocarcinoma cell line; BxPC3: human pancreatic adenocarcinoma cell line; KB: human oral carcinoma cell line; KB-V1: vinblastine-resistant human cervix carcinoma cell line; LoVo: human colon adenocarcinoma cell line; Namalwa: Burkitt lymphoma cell line; and SkoV3: human ovarian adenocarcinoma cell line).

The cells are seeded in 96-well plates in phenol red-free RPMI 1640 medium (Seromed) to which is added 10% fetal calf serum (100 μl/well, 1·10$^4$ to 3·10$^4$ cells/ml depending on the line studied). After incubation for 24 hours at 37° C. in an incubator (5% CO$_2$), the medium is replaced with the same medium further containing the compound to be tested (various concentrations are used) and then the plates are incubated for an additional 48 hours. Cell survival is evaluated by measuring luminescence after ATP release in the medium using the cell lysis solutions, luciferase and luciferin, included in the ATP-lite-M™ kit as recommended by the manufacturer (Packard, Rungis, France). Each experimental condition was tested at least three times in sextuplicate.

The results obtained are presented in the following table.

| Molecule | \multicolumn{7}{c}{$EC_{50}$ for various tumor cell lines (in M)} |
|---|---|---|---|---|---|---|---|
|  | A549 | BxPC3 | KB | KB-V1 | LoVo | Namalwa | SkoV3 |
| (I-1) | $1.1 \cdot 10^{-11}$ | $2.2 \cdot 10^{-10}$ | $3.1 \cdot 10^{-10}$ | $7.0 \cdot 10^{-10}$ | $4.0 \cdot 10^{-11}$ | $3.1 \cdot 10^{-10}$ | $3.6 \cdot 10^{-5}$ |
| (I-2) | $<10^{-12}$ | $2.1 \cdot 10^{-10}$ | $3.0 \cdot 10^{-10}$ | $4.9 \cdot 10^{-10}$ | $1.1 \cdot 10^{-11}$ | $3.6 \cdot 10^{-10}$ | $1.3 \cdot 10^{-6}$ |
| (I-3) | $<10^{-12}$ | $1.2 \cdot 10^{-11}$ | $2.4 \cdot 10^{-11}$ | $7.3 \cdot 10^{-10}$ | $<10^{-11}$ | $3.2 \cdot 10^{-10}$ | $3.2 \cdot 10^{-7}$ |

The invention claimed is:

1. A method for treating cancer which comprises administering to a person in need thereof of an effective dose of a compound of the following formula (I)

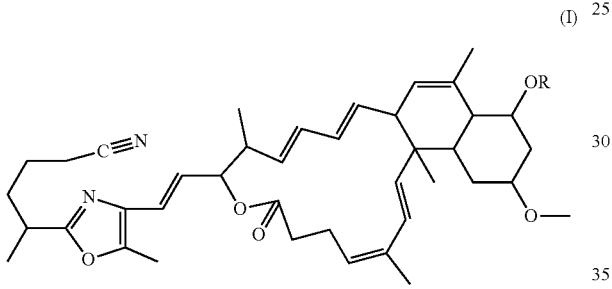

(I)

or a pharmaceutically acceptable salt, hydrate or solvate thereof, in which R is a monosaccharide or disaccharide residue, the hydroxyl functional groups of the monosaccharide or disaccharide residue being, independently of each other, optionally substituted with a ($C_1$-$C_6$)alkyl group or a —C(O)NH—($C_1$-$C_6$)alkyl group.

2. A method for treating cancer which comprises administering to a person in need thereof of an effective dose of a pharmaceutical composition comprising a pharmaceutically acceptable excipient and at least one compound of the following formula (I):

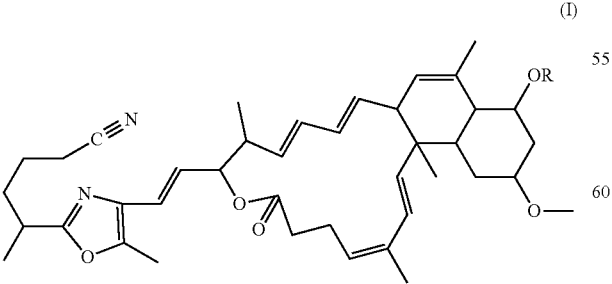

(I)

or a pharmaceutically acceptable salt, hydrate or solvate thereof, in which R is a monosaccharide or disaccharide residue, the hydroxyl functional groups of the monosaccharide or disaccharide residue being, independently of each other, optionally substituted with a ($C_1$-$C_6$)alkyl group or a —C(O)NH—($C_1$-$C_6$)alkyl group.

3. The method according to claim 1, wherein R is a monosaccharide or disaccharide residue, the hydroxyl functional groups of the monosaccharide or disaccharide residue being, independently of each other, optionally substituted with a methyl group or a —C(O)NHMe group.

4. The method according to claim 1, wherein R is the following group:

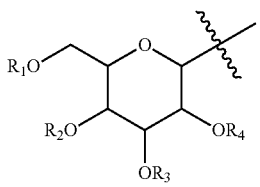

in which the $R_1$ to $R_4$ groups are, independently of each other, a hydrogen atom, a ($C_1$-$C_6$)alkyl group, a —C(O)NH—($C_1$-$C_6$)alkyl group, or a monosaccharide residue of the following formula:

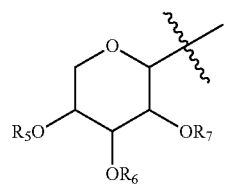

in which the $R_5$ to $R_7$ groups are, independently of each other, a hydrogen atom, a ($C_1$-$C_6$)alkyl group or a —C(O)NH—($C_1$-$C_6$)alkyl group, wherein only one $R_1$ to $R_4$ group may be a monosaccharide residue.

5. The method according to claim 4, wherein the ($C_1$-$C_6$) alkyl group is a methyl group and the —C(O)NH—($C_1$-$C_6$) alkyl group is a —C(O)NHMe group.

6. The method according to claim 4, wherein $R_1$=$R_4$=Me, $R_2$=H and $R_3$=H or a monosaccharide residue of the following formula:

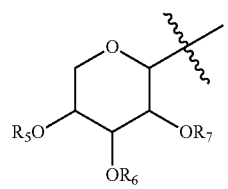

with $R_5$ to $R_7$ as defined in claim 4.

7. The method according to claim 4, wherein R is a:

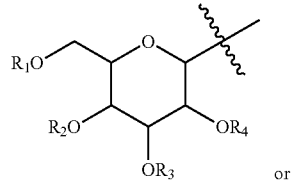

or

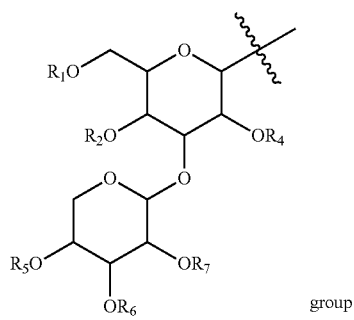

group in which:

R$_1$ to R$_4$ are, independently of each other, a hydrogen atom, a (C$_1$-C$_6$)alkyl group or a —C(O)NH—(C$_1$-C$_6$)alkyl group, and R$_5$ to R$_7$ are, independently of each other, a hydrogen atom, a (C$_1$-C$_6$)alkyl group or a —C(O)NH—(C$_1$-C$_6$)alkyl group.

8. The method according to claim 7, wherein R is a group selected from:

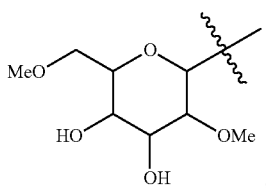,

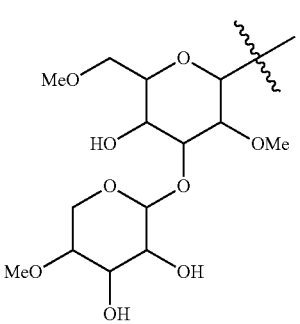

and

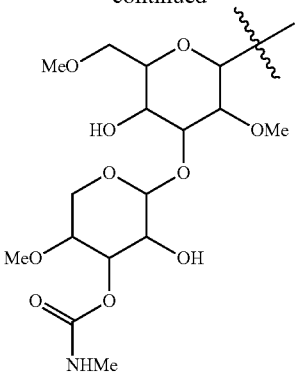

9. The method according to claim 1, wherein the compound of formula (I) is obtained by a method comprising the following successive steps:
(i) macerating a lyophilizate of a sponge of the family Verongidae one or more times with a water/ethanol solution; followed by filtering the maceration medium or media to yield a filtrate; then concentrating said filtrate to yield an aqueous syrup,
(ii) adding water to the aqueous syrup obtained in the preceding step (i), extracting with ethyl acetate one or more time and separating the resulting aqueous and organic phases; concentrating the organic phase or the combined organic phases thus obtained to yield a dry extract,
(iii) isolating from the dry extract obtained in the preceding step (ii) a compound of formula (I) according to claim 1 with R being:

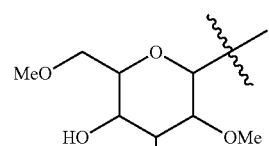,

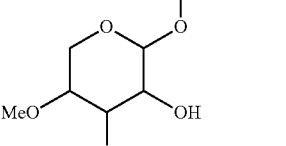

or

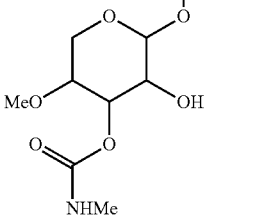, (iv) optionally hydrolyzing the compound of formula (I) obtained in the preceding step to yield a compound of the following formula (II):

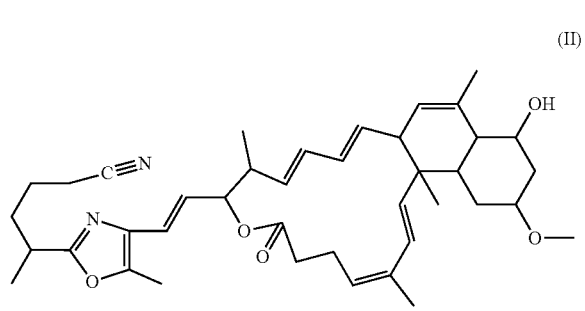 [SMILES: COC1CC(O)C2C(C)=CC3/C=C/C=C/C(C)C(/C=C/c4nc(C(C)CCCC#N)oc4C)OC(=O)CC/C=C(C)\C=C\C3(C)C2C1]

(II)

and substituting the OH functional group of the compound of formula (II) to yield a compound of formula (I) as defined in claim 1, and (v) optionally salifying, hydrating or solvating the compound of formula (I) obtained in the preceding step (iii) or (iv) to yield a pharmaceutically acceptable salt, hydrate or solvate thereof.

10. The method according to claim 9, wherein, the sponge is a *Suberea* sp. sponge.

11. The method according to claim 10, wherein, the sponge is *Suberea creba*.

12. The method according to claim 1, wherein the compound of formula (I) is selected from:

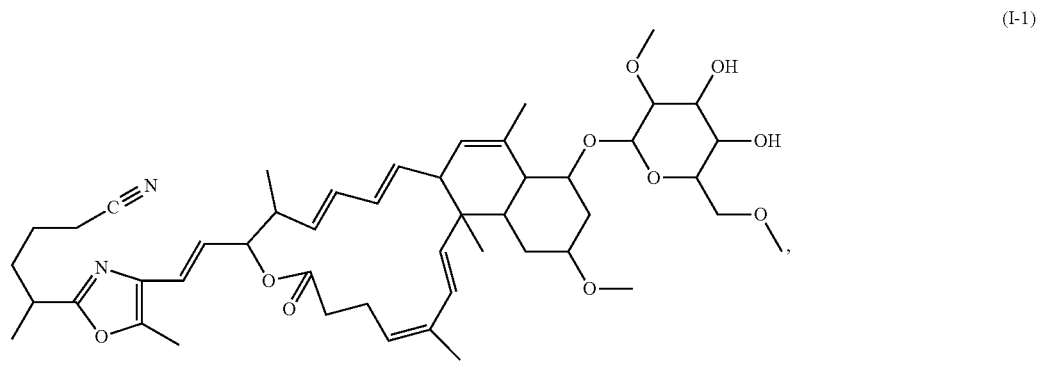

(I-1)

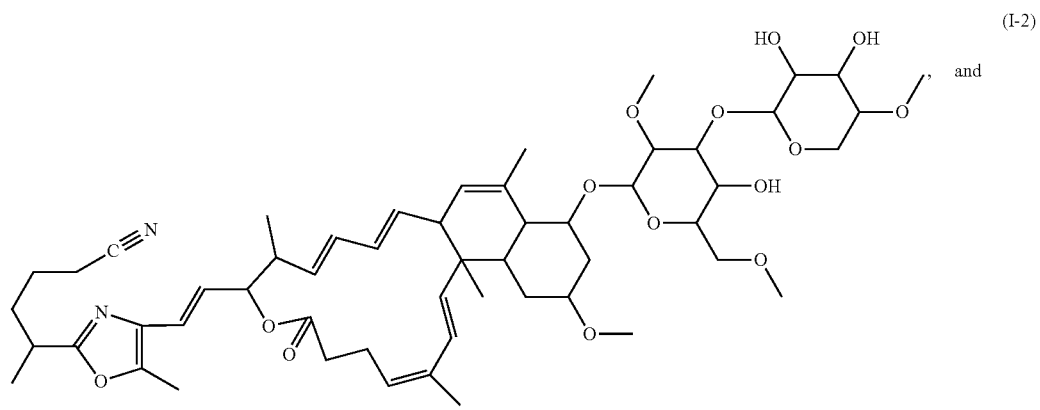

(I-2)

and

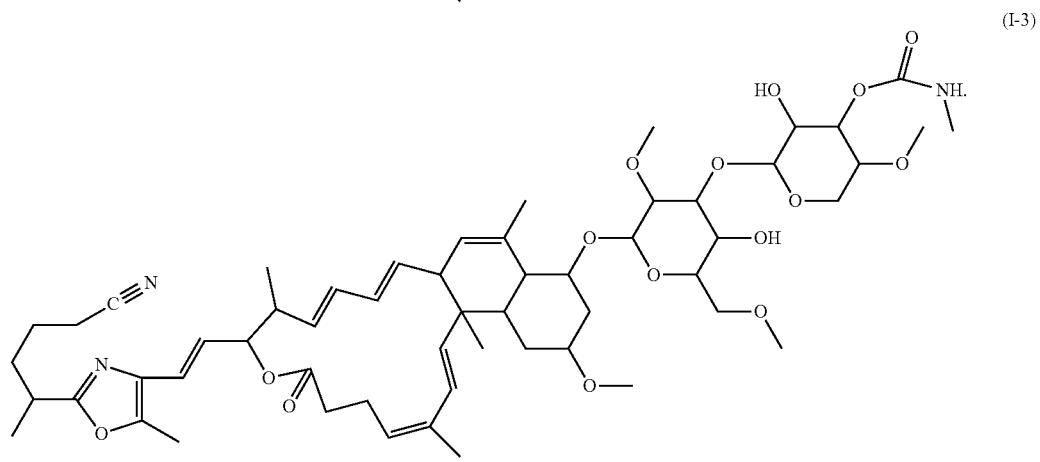

(I-3)

13. The method according to claim 1, wherein the cancer is selected from melanoma, colorectal cancer, lung cancer, prostate cancer, liver cancer, breast cancer, uterine cancer, stomach cancer, pancreatic cancer, bladder cancer, ovarian cancer, head and neck cancers, brain cancer, leukemia, lymphomas and myelomas.

14. The method according to claim 2, wherein R is the following group:

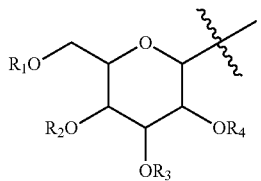

in which the $R_1$ to $R_4$ groups are, independently of each other, a hydrogen atom, a $(C_1\text{-}C_6)$alkyl group, a —C(O)NH—$(C_1\text{-}C_6)$alkyl group, or a monosaccharide residue of the following formula:

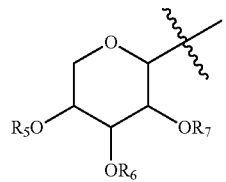

in which the $R_5$ to $R_7$ groups are, independently of each other, a hydrogen atom, a $(C_1\text{-}C_6)$alkyl group or a —C(O)NH—$(C_1\text{-}C_6)$alkyl group, wherein only one $R_1$ to $R_4$ group may be a monosaccharide residue.

15. The method according to claim 14, wherein $R_1=R_4=$Me, $R_2=$H and $R_3=$H or a monosaccharide residue of the following formula:

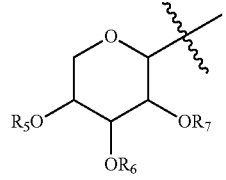

with $R_5$ to $R_7$ as defined in claim 14.

16. The method according to claim 14, wherein R is a:

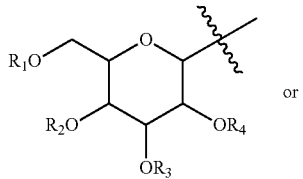

or

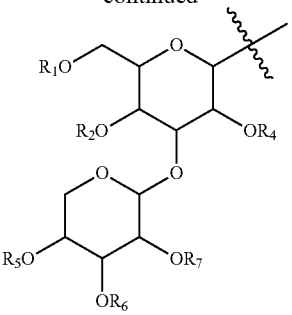

group
in which:
$R_1$ to $R_4$ are, independently of each other, a hydrogen atom, a $(C_1\text{-}C_6)$alkyl group or a —C(O)NH—$(C_1\text{-}C_6)$alkyl group, and
$R_5$ to $R_7$ are, independently of each other, a hydrogen atom, a $(C_1\text{-}C_6)$alkyl group or a —C(O)NH—$(C_1\text{-}C_6)$alkyl group.

17. The method according to claim 2, wherein the compound of formula (I) is obtained by a method comprising the following successive steps:
(i) macerating a lyophilizate of a sponge of the family Verongidae one or more times with a water/ethanol solution; followed by filtering the maceration medium or media to yield a filtrate; then concentrating said filtrate to yield an aqueous syrup,
(ii) adding water to the aqueous syrup obtained in the preceding step (i), extracting with ethyl acetate one or more times and separating the resulting aqueous and organic phases; concentrating the organic phase or the combined organic phases thus obtained to yield a dry extract,
(iii) isolating from the dry extract obtained in the preceding step (ii) a compound of formula (I) according to claim 2 with R being:

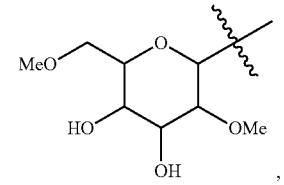

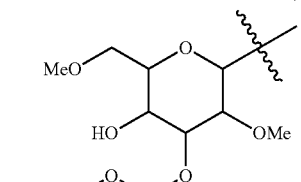

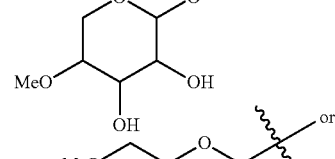 or

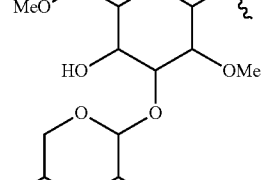

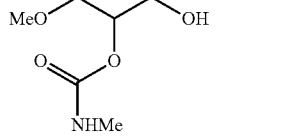

(iv) optionally hydrolyzing the compound of formula (I) obtained in the preceding step to yield a compound of the following formula (II):

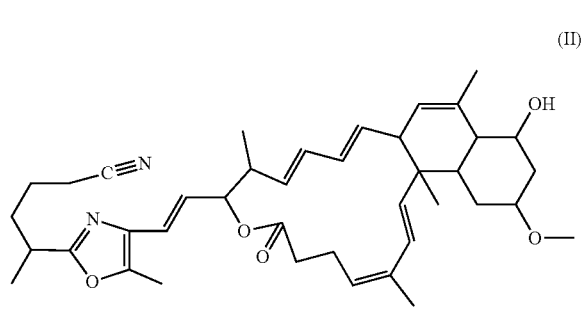 [SMILES: COC1CC(O)C2C(C)=CC3/C=C/C=C/C(C)C(/C=C/c4nc(C(C)CCCC#N)oc4C)OC(=O)CC/C=C(C)\C=C\C3(C)C2C1]

and substituting the OH functional group of the compound of formula (II) to yield a compound of formula (I) as defined in claim 2, and (v) optionally salifying, hydrating or solvating the compound of formula (I) obtained in the preceding step (iii) or (iv) to yield a pharmaceutically acceptable salt, hydrate or solvate thereof.

18. The method according to claim 17, wherein, the sponge is *Suberea creba*.

19. The method according to claim 2, wherein the compound of formula (I) is selected from:

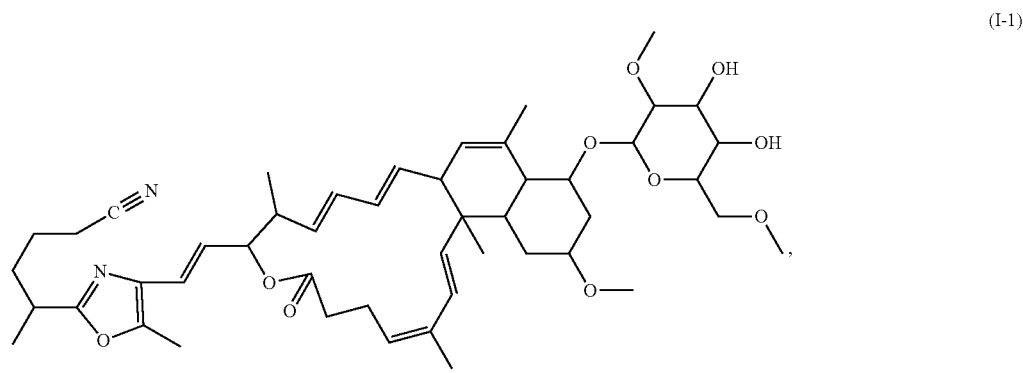

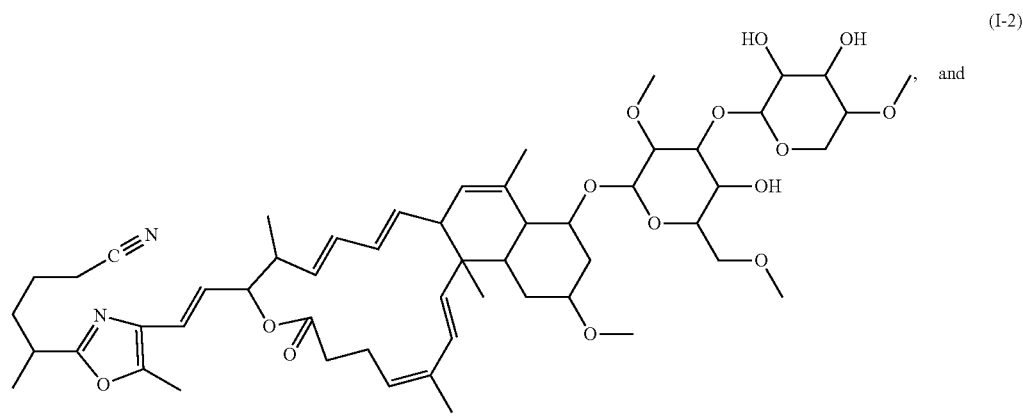

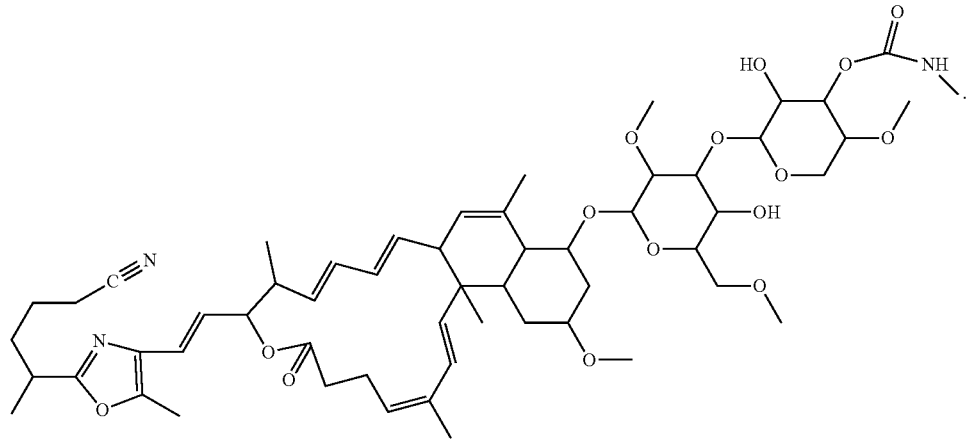
20. The method according to claim 2, wherein the cancer is selected from melanoma, colorectal cancer, lung cancer, prostate cancer, liver cancer, breast cancer, uterine cancer, stomach cancer, pancreatic cancer, bladder cancer, ovarian cancer, head and neck cancers, brain cancer, leukemia, lymphomas and myelomas.
* * * * *